(12) United States Patent
Ramachandran et al.

(10) Patent No.: US 9,405,085 B2
(45) Date of Patent: Aug. 2, 2016

(54) SMART TOOL HOLDER FOR AN OPTICAL SHAPE-SENSING FIBER

(71) Applicant: KONINKLIJKE PHILIPS N.V., Eindhoven (NL)

(72) Inventors: Bharat Ramachandran, Morganville, NJ (US); Robert Manzke, Bonnebuttel (DE); Raymond Chan, San Diego, CA (US)

(73) Assignee: Koninklijke Philips N.V., Eindhoven (NL)

( * ) Notice: Subject to any disclaimer, the term of this patent is extended or adjusted under 35 U.S.C. 154(b) by 159 days.

(21) Appl. No.: 14/353,830

(22) PCT Filed: Oct. 17, 2012

(86) PCT No.: PCT/IB2012/055646
§ 371 (c)(1),
(2) Date: Apr. 24, 2014

(87) PCT Pub. No.: WO2013/061212
PCT Pub. Date: May 2, 2013

(65) Prior Publication Data
US 2014/0308016 A1 Oct. 16, 2014

Related U.S. Application Data

(60) Provisional application No. 61/551,499, filed on Oct. 26, 2011.

(51) Int. Cl.
*G02B 6/44* (2006.01)
*G02B 6/42* (2006.01)
*A61B 10/04* (2006.01)
*A61B 17/34* (2006.01)
*A61B 17/00* (2006.01)

(52) U.S. Cl.
CPC ............. *G02B 6/4439* (2013.01); *G02B 6/42* (2013.01); *A61B 10/04* (2013.01); *A61B 17/3478* (2013.01); *A61B 2017/00362* (2013.01); *A61B 2017/00464* (2013.01); *A61B 2017/00482* (2013.01); *A61B 2034/2068* (2016.02)

(58) Field of Classification Search
CPC .... G02B 6/42; G02B 6/4439; A61B 19/5244; A61B 2019/5261
See application file for complete search history.

(56) References Cited

U.S. PATENT DOCUMENTS

| 7,772,541 | B2* | 8/2010 | Froggatt | G01M 11/083 |
| | | | | 250/226 |
| 9,285,246 | B2* | 3/2016 | Prisco | A61B 19/2203 |
| 2003/0055409 | A1 | 3/2003 | Brock | |
| 2005/0199250 | A1 | 9/2005 | Green, II et al. | |
| 2007/0156019 | A1* | 7/2007 | Larkin | A61B 19/2203 |
| | | | | 600/104 |
| 2008/0287963 | A1 | 11/2008 | Rogers et al. | |
| 2009/0123111 | A1 | 5/2009 | Udd | |
| 2009/0324161 | A1 | 12/2009 | Prisco | |

(Continued)

FOREIGN PATENT DOCUMENTS

WO    WO2012046202    4/2012

*Primary Examiner* — Daniel Petkovsek

(57) ABSTRACT

A method, system, and program product hold and manipulate tools during an intervention procedure. The device comprises: a holder body in fixed attachment with a shape-sensing fiber optic fiber; one of a plurality of tools being held by the holder body in coupled alignment with the shape-sensing fiber optic fiber.

14 Claims, 4 Drawing Sheets

(56) References Cited

U.S. PATENT DOCUMENTS

2010/0048998 A1 2/2010 Younge et al.
2010/0076455 A1 3/2010 Birkenbach et al.
2010/0082041 A1 4/2010 Prisco
2010/0249507 A1 9/2010 Prisco et al.

* cited by examiner

SMART TOOL HOLDER FOR AN OPTICAL SHAPE-SENSING FIBER

CROSS-REFERENCE TO PRIOR APPLICATIONS

This application is the U.S. National Phase application under 35 U.S.C. §371 of International Application Serial No. PCT/IB2012/055646, filed on Oct. 17, 2012, which claims the benefit of U.S. Application Ser. No. 61/551,499, filed on Oct. 26, 2011. These applications are hereby incorporated by reference herein.

FIELD OF THE INVENTION

The invention relates to the field of medical image guided intervention and more particularly to a smart tool holder for an optical shape sensing fiber for use in intervention or surgical procedures.

BACKGROUND

Fiber optic shape sensing (OSS) systems are very valuable for device tracking since they provide 3D position and shape information along the entire length of a device. This, for example, allows the instrument to be registered to intra-operative or preoperative medical images, thereby assisting guided navigation during an intervention or surgical procedure.

Due to a small fiber footprint (less than ~400 μm), OSS enabled devices can be used for navigation in endovascular and endoluminal interventions, which involve passing through vessels and lumens of small diameters. This small footprint also allows OSS enabled devices to access, minimally invasively, areas such as peripheral airways, which a standard scope cannot reach.

However, merely reaching a target is not the end goal, and in most medical procedures, following the navigation step, an action, such as a biopsy or drug delivery is performed. Present OSS enabled devices are not suited to performing such actions.

SUMMARY

A device and method are provided for holding tools during an intervention procedure. The device comprises: a holder body in fixed attachment with a shape-sensing fiber optic fiber; one of a plurality of tools held by said holder body in coupled alignment with said shape-sensing fiber optic fiber.

According to one embodiment, at least two tools are used and held at the same time. In one embodiment, at least one tool is a sensor, and another tool is deployed in response to readings from said sensor.

According to one embodiment the one of a plurality of tools is operated by the tool holder. The holder body may deploy or other wise operate the tool in response to a manual input from a user, in response to a signal generated by a user through a workstation or a direct input device, or in response to a signal from a sensor on or held by the holder body.

According to one embodiment, the tool holder further comprising a logic device, wherein said logic device activates said one of a plurality of tools. The activation may comprise extending said tool from said holder body. Alternatively, the activation may comprise powering a tool action.

According to one embodiment a plurality of tools are stored in the holder body and one of the plurality of tools is deployed through the chuck by an actuator. The actuator may be triggered by an optical signal through said shape-sensing fiber optic fiber.

According to one embodiment the device may further comprise a processing device and a sensor, wherein the plurality of tools comprise identification, and the sensor senses the identification on the one of said tools held in the chuck and sends the identification to the processing device to identify the one of the plurality of tools held in the chuck. In one embodiment the processing device uses the identifications to select a one of said tools.

According to one embodiment, the holder body comprises a photo transceiver adjacent a distal end of the optic fiber for sending and receiving data through the optic fiber.

According to one embodiment, the holder body comprises a chamber for collecting samples.

According to one embodiment the holder body is about the same size as said fiber optic fiber.

According to another aspect of the present invention, a system is provided for performing as medical intervention, the system comprises: a shape sensing fiber optic tether, a tool holder fixed to a distal end of said shape-sensing fiber optic fiber, at least one processor, at least one memory operably connected with the at least one processor, and at least one tool held by the holder body in coupled alignment with the fiber optic tether, wherein the processor initiates an action at the at least one tool.

According to one embodiment the action is a motion of the at least one tool. Alternatively, the action may be powering the at least one tool. According to another embodiment, the action is selection of one of the at least one tools. According to another embodiment, the action is communication of data from the at least one tool.

In other embodiments, other actions and various combinations of actions may be initiated by the processor.

According to another aspect of the present invention, a method is provided for performing an intervention with a tool holder fixed to a distal end of a shape sensing optic fiber. The method comprises: receiving a stimulus to perform a tool action; and triggering the tool action.

According to one embodiment, the stimulus is a command initiated by a user. According to another embodiment, the stimulus is a reading from a sensor attached to the tool holder.

According to one embodiment, the action is a motion of the at least one tool. According to other embodiments, the action may be: powering the at least one tool, selection of one of the at least one tool, and communication of data from the at least one tool.

According to one embodiment, the tool action is performed with the holder body external to a patient. According to other embodiments, the tool action is performed with the holder body internal to a patient and with the holder body partially internal to a patient.

BRIEF DESCRIPTION OF THE DRAWINGS

The features and advantages of the invention will be more clearly understood from the following detailed description of the preferred embodiments when read in connection with the accompanying drawing. Included in the drawing are the following figures.

DETAILED DESCRIPTION

Figure 1:
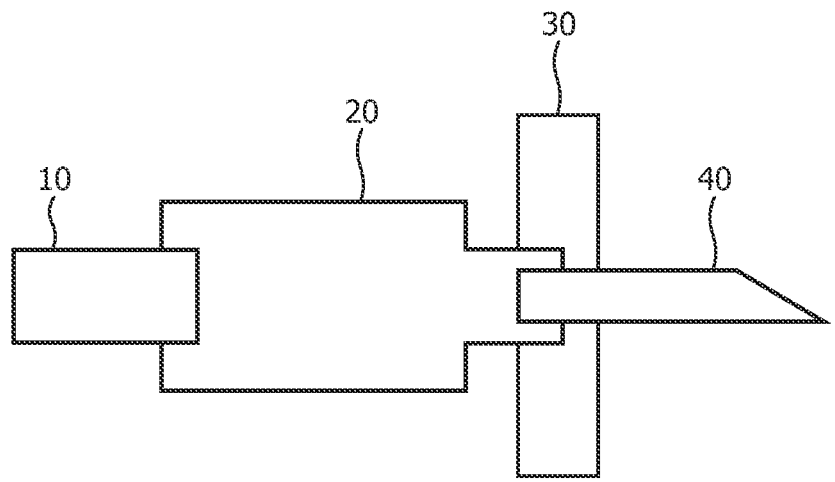
FIG. 1 is a sectional view of a device for holding tools during an intervention procedure according to one embodiment of the present invention.

The present invention provides a device and method for holding tools during an intervention procedure. According to one embodiment, a tool holder body 20 is affixed to an OSS enabled tether 10. The tool holder body 20 may be about the same size or smaller than the fiber optic tether 10 to allow for navigation through small vessels/lumens or to allow for access to peripheral airways and the like.

The holder body 20 may be affixed to the fiber optic tether 10 by any suitable attachment means, such as mechanical, pneumatic, electromagnetic crimping, clamping, adhesive, molding, or any other appropriate fixation technique.

Opposite the fiber optic tether 10, one tool 40 of a plurality of tools is interchangeably held by the holder body 20 in coupled alignment with the shape-sensing fiber optic tether 10. According to one embodiment the tool is held in coupled alignment by a chuck 30. The chuck 30 may be attached to the holder body 20 by threaded engagement, soldering, adhesive, molding or any other suitable attachment technique. The chuck 30 may be a collet chuck, a fingered chuck, a magnetic chuck, a vacuum chuck or any other type of chuck suitable for holding a surgical tool in coupled attachment with a fiber optic fiber.

The tool 40 may be a tool for cutting, such as a blade, a scalpel, scissors, or the like. The tool 40 may alternatively be a tool for collecting a sample or biopsy or for draining fluid, such as a forceps, brush, hook or curvature, a suction device, or the like. The tool 40 may alternatively be a needle or the like for injecting drugs, stem cells, or the like. The tool 40 may be an expanding device, such as a balloon or expanding mesh for enlarging a lumen or for lumen creation within a tissue or organ. The tool 40 may be a sensing/imaging device, such as a camera, an ultrasound transceiver, or the like. The tool 40 may also be a pointer detectable by an external imaging system for pointing at structures or for registration. The tool 40 may also be an ablation tool delivering heat, radio frequency energy, laser, electrical energy, or any other energy source suitable for endoluminal, endovascular, or other internal ablation procedures. The tool 40 may also be a shaping, forming, or routing device, such as a drill for drilling holes in a planned and controlled direction, a grinding bit for contouring or surfacing in orthopedic or dental applications. The plurality of tools may include any combination of the aforementioned tools and/or any other tools suitable for use in an intervention procedure. Different tools may be used during a procedure or in different procedures with the same OSS fiber and holder body, reducing the cost associated with the shape sensing fiber optic fiber.

The tools may be removably or permanently attached to the holder body 20. Also, the tools may be re-usable or disposable, and may be attachable to the distal tip of different OSS fibers.

According to an alternative embodiment, one or more tools may be held, either removably or permanently by the tool holder body 20 by alternative holding means, such as: being integrally molded with the holder body 20, being integrally machined into the holder body, being attached to the holder body using adhesive, threaded engagement, or any other mechanical, chemical, pneumatic, or electromagnetic, or other fixation technique suitable for temporary or permanent attachment.

Figure 2:
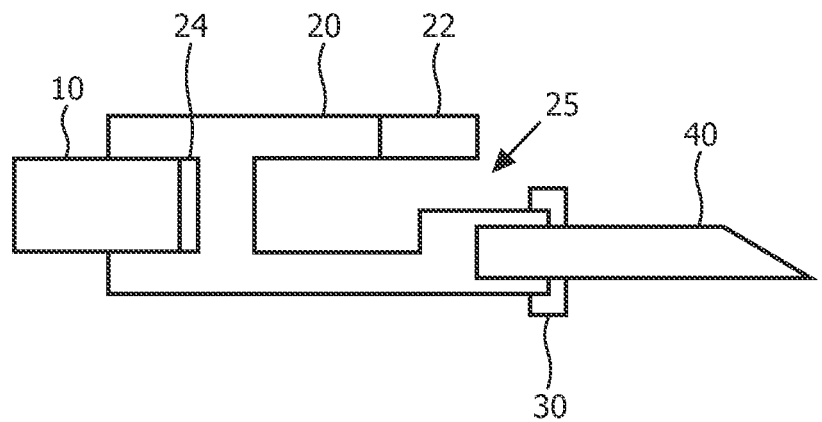
FIG. 2 is a sectional view of a device for holding tools during an intervention procedure according to another embodiment of the present invention.

As shown in FIG. 2, a plurality of tools 22, 40 may be held by the holder body 20 at the same time. In the illustrated example, a permanent integral tool 22, such as a sensor or suction tool is held by permanent attachment or is held by being integrally formed or machined into the holder body 20. At the same time, another tool 40, which may be, by way of example, a scalpel for cutting, is held by the holder body using a chuck 30. Thus, while the scalpel 40 makes a cut, the first tool 22 may be a sensor sensing the location for the cut, or sensing the completion of the cut, or may be a suction tool for capturing the cut tissue. As will be understood by those skilled in the art, the foregoing are only a few examples of the various combinations of tools that would be useful on a OSS enabled device for various medical intervention procedures.

According to one embodiment, the holder body 20 may further comprise a sterile chamber 25 for collecting samples of tissue or fluids, as shown in FIG. 2. For example, a suction tool may be used to extract a sample of fluid or a sample of tissue that was cut, and the sample may be stored in the chamber 25 until it is drained during or following the intervention.

Figure 3:
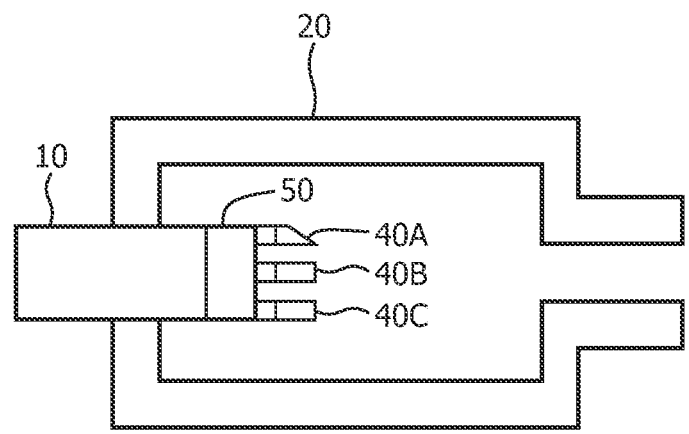
FIG. 3 is a sectional view of a device for holding tools during an intervention procedure according to another embodiment of the present invention.
Figure 4:
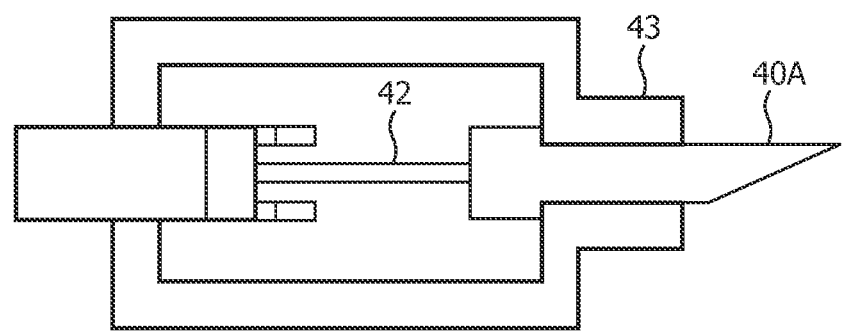
FIG. 4 is a sectional view of the device of FIG. 3 with one of a plurality of tools deployed.

According to another embodiment, a tool holder 20 attached to a OSS-enabled tether 10 may include one or more deployable tools. As shown in FIG. 3, one or more tools 40A, 40B, 40C may be disposed on an actuation device 50 within the holder body 20. The actuation device may comprise one or more actuators 42, such as springs, solenoids, or the like to manipulate a selected tool 40A into coupled alignment with the fiber optic fiber 10 through a holding means 32, such as a tapered collet or the like, as shown in FIG. 4

The actuation device 50 may deploy a selected tool 40A in response to a manual user input, a user input signal, a signal from an imaging system, or a signal from a sensor comprising another tool affixed to the holder body 20. According to one embodiment, a user provides an input to deploy a selected tool 40A, such as when the user determines that the holder body has been successfully navigated to an intervention target. The user input may be transmitted through the fiber optic fiber or through a wired or wireless signal, or through any other suitable transmission means.

The manual user input may comprise, for example, pushing or pulling a release mechanism or a wire attached to a release mechanism holding the selected tool in an undeployed position in the holder body.

According to another embodiment, the actuation device 50 includes or is operably connected with a logic device that determines when to deploy the selected tool 40A and triggers the actuation. The logic device may be internal to the holder body 20 or may be a workstation communicating with the actuation device, through the fiber optic fiber, wireless transmission, or any other suitable communication means. The logic device may determine when to deploy a selected tool 40A based on readings from a sensor that is one of the tools held by the holder body 20, or based on calculations from an imaging system, such as determination from the shape sensing that the holder body 20 is at a target location. According to one embodiment, the logic device may be one or more processors, such as microprocessors, programmable logic devices, such as EPROMS/EEPROMs, or any other suitable device. The actuation device may be triggered by a wired or wireless signal form the logic unit, time activation, magnetic activation, light activation, or any combination thereof.

According to one embodiment, the tools 40A, 40B, etc. have an identification that can be read by the holder body 20 to identify a selected tool. The identification may be an etched or painted marking, an RFID chip, a magnetic identification, or any other identification suitable for reading with optical, radio frequency, magnetic or any other sensor that can be located in the holder body 20.

The identification may be combined with a data library stored in a memory in the tool holder 20, accessible to the tool holder, or in a workstation in communication with the tool holder, or accessible to a workstation in communication with the tool holder. The library may comprise data for accurately representing the selected tool on an imaging system, for example. Also, the data may be used to optimize calibration, registration, or other usage of the tool in combination with the imaging and monitoring environment.

According to one embodiment a data storage device may be attached to or be integral with each tool. The data storage device may store data about the tool, such as tool identification and tool configuration for use in tip extrapolation and to accurately representing the tool on the OSS or other imaging display. To read the data on the data storage device, the tool holder may be equipped with an appropriate sensor, such as an optical scanner, which may be located in the actuation device 50, for example, to read a data storage device at the back end of each tool.

According to one embodiment, the tool holder 20 is equipped with a photodetector 24, as shown in FIG. 2, for receiving communication signals through the fiber optic fiber 10. The photo detector 24 could also be a photo transceiver, both receiving and sending signals at the holder body 20, allowing communication to and from a OSS imaging workstation. The photo detector or photo transceiver is positioned adjacent the distal tip of the optic fiber to send and receive optical signals to and from the fiber.

A logic device and sensor may be used to select, deploy, extend, retract, change, and operate various tools in the tool holder body 20. For example, a user command may be sent through the optic fiber 10 to a photo detector 24 shown in FIG. 2. The photodetector may then send the command signal to the logic device, which uses data storage devices on the tools to locate the identified tool and trigger the corresponding actuation device 50 to deploy the selected tool identified in the command. Also, a sensor located near the back end of each tool can sense identification and other data about the tool and provide that data to the logic device. For example, temperature data may be received from a thermistor tool which can be provided to the logic device and used to determine when to stop an ablation tool, for example.

Alternatively, the logic device may be operatively connected to a decision support database, so that the logic device selects or proposes specific tools based on application specific requirements and/or information in real time.

A selected tool may be deployed or operated while the holder body is external to a patient, internal to a patient, or partially external to a patient.

Figure 5:
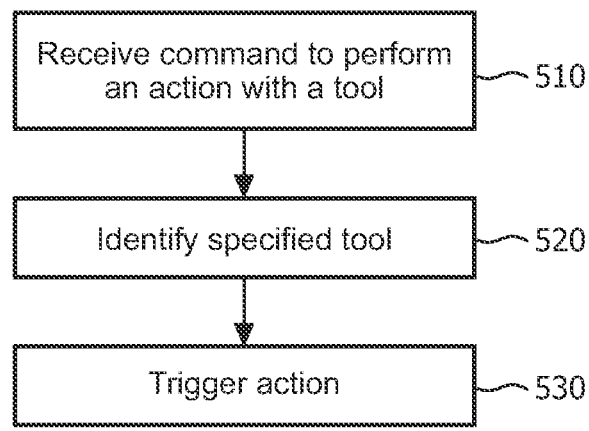
FIG. 5 is a flow diagram of a method for performing an intervention with a remotely triggered tool action according to an embodiment of the present invention.

FIG. 5 is a flow diagram of a method for performing an intervention with a remotely triggered tool action according to an embodiment of the present invention. A logic device 830, shown in FIG. 8, such as a microprocessor, receives a signal to perform a tool action (Step 510). The action may be to deploy, extend, retract, initiate, stop, or change a tool, or it may be any other action that may be performed by a tool. The signal may be a user initiated electronic signal transmitted through a wired connection or a wireless connection 850 or a user initiated optical signal transmitted over the fiber optic fiber 10 to a photodetector 24 operably connected to the logic device 830. Alternatively, the signal may be initiated by the OSS workstation, based on image analysis and communicated to the photodetector 24 or connection 850 by any suitable means.

Where more than one tool is held by the tool holder 20, the signal may indicate or specify which tool is to perform an action. The logic device 830 identifies the specified tool (Step 520). That is, the logic device 830 uses one or more sensors 820 to read data 810 from the tools. The data may be a marking painted or etched onto the back of the tool, digital data stored in a data storage device attached to the back of the tool, an RFID chip attached to the back of the tool or any other form suitable for storing data on the tool. The sensor 820 is an optical scanner, wired or wireless connector, RFID receiver, or other sensor suitable for retrieving the data 810 from the tool.

The logic device triggers the appropriate tool action (Step 530). According to one embodiment, the logic device 830 is operably connected with an actuator 50 and the logic device 830 sends a signal that causes the actuator to actuate. For example, the signal may cause a spring actuator to release a lock causing the spring to extend and push the tool into an extended position. Alternatively, the signal may trigger a solenoid to actuate and extend or retract the tool, or push a plunger of an injection tool, or open or close a gripping tool. According to other embodiments, the signal may turn on an electric motor for a drill tool or for a suction tool, turn on power for an ablation tool, change tools, initiate any other suitable tool action.

Figure 6:
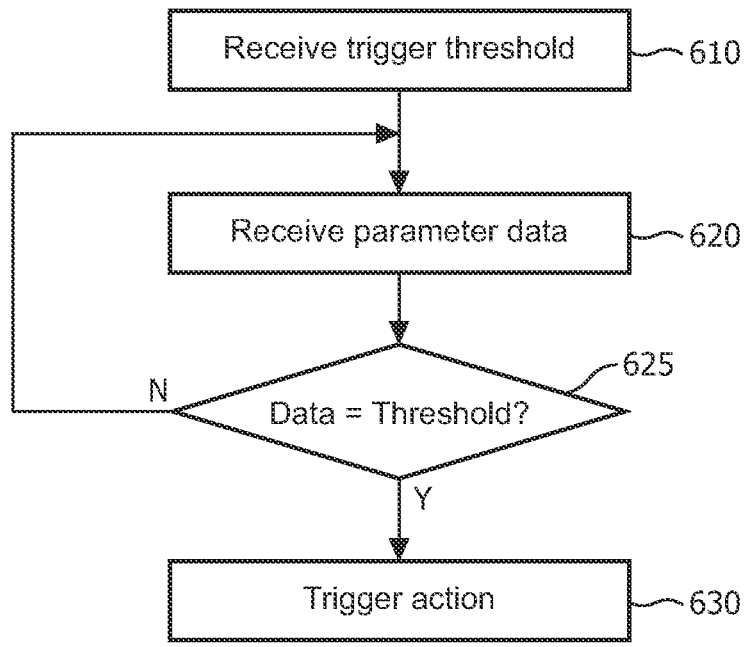
FIG. 6 is a flow diagram of a method for performing an intervention with an automatically triggered action according to an embodiment of the present invention.

FIG. 6 is a flow diagram of a method for performing an intervention with an automatically triggered action according to an embodiment of the present invention. The logic device 830 receives a triggering threshold (Step 610). The triggering threshold may be received, for example, from the OSS workstation, from another processing device, directly from a user input, or any other suitable source. The triggering threshold may be a sensor reading for a sensor tool in the tool holder 20, a period of time, or any other suitable parameter for a tool action.

The logic device 830 receives parameter data (Step 620). The parameter data may be sensor readings, elapsed time from a timing circuit, or other suitable data.

The logic device 830 compares the parameter data to the threshold (Step 625). If the data meets the threshold, then the logic device triggers a tool action (Step 630). If the data does not meet the threshold, then the logic device continues to compare the data to the threshold (Step 625).

Figure 7:
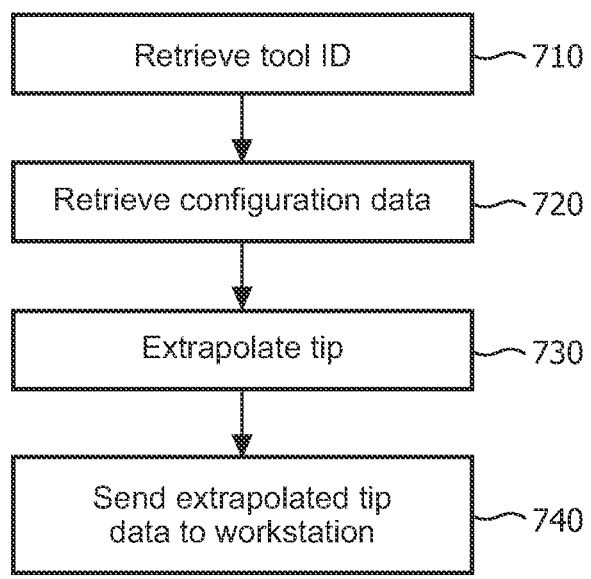
FIG. 7 is a flow diagram of a method for performing an intervention with a communication between a smart tool holder and a OSS workstation according to an embodiment of the present invention.
Figure 8:
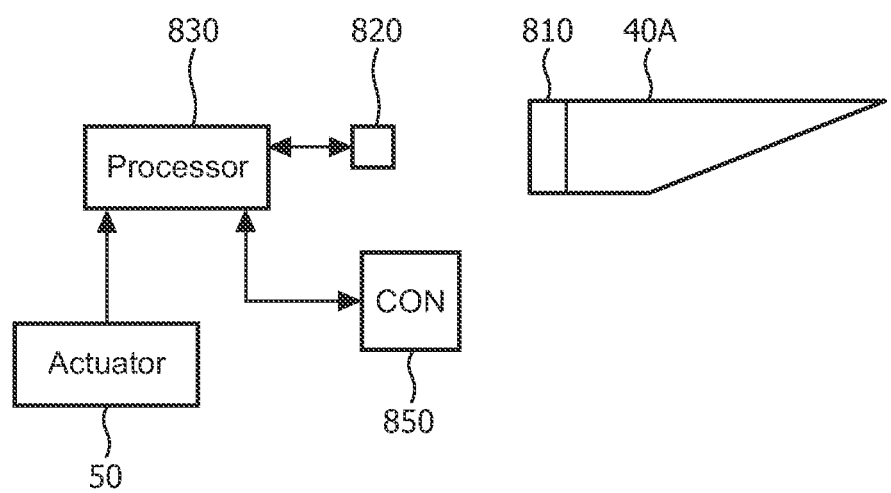
FIG. 8 is a block diagram of a smart tool holder according to an embodiment of the present invention.

FIG. 7 is a flow diagram of a method for performing an intervention with a communication between a smart tool holder and a OSS workstation according to an embodiment of the present invention. The logic device 830 retrieves a tool identification (Step 710). The tool identification may be retrieved from the tool using sensor 820. The logic device 830 also retrieves configuration data from a tool configuration database (Step 720). Using the configuration data, the logic device extrapolates the location of the tip of the tool relative to the distal tip of the shape sensing fiber (Step 730). The logic device sends the extrapolated tip data to the OSS work station (Step 740). The tip data may be sent to the workstation through the optic fiber as optical data via a photo transceiver 24 or through another connection 850 (FIG. 8). Alternatively, the data may be sent from the logic device 830 to the OSS workstation or any other processing device through a wired or wireless connector. Similarly, data may be sent from the OSS workstation or any other processing device to the logic device 830 in the tool holder body 20 through a photo transceiver 24 or other connection 850.

The invention can take the form of an entirely hardware embodiment or an embodiment containing both hardware and software elements. In an exemplary embodiment, the invention is implemented in software, which includes but is not limited to firmware, resident software, microcode, etc.

Furthermore, the invention may take the form of a computer program product accessible from a computer-usable or computer-readable medium providing program code for use by or in connection with a computer or any instruction execution system or device. For the purposes of this description, a computer-usable or computer readable medium may be any apparatus that can contain or store the program for use by or in connection with the instruction execution system, apparatus, or device.

The foregoing method may be realized by a program product comprising a machine-readable medium having a machine-executable program of instructions, which when executed by a machine, such as a computer, performs the steps of the method. This program product may be stored on any of a variety of known machine-readable medium, including but not limited to compact discs, floppy discs, USB memory devices, and the like.

The medium can be an electronic, magnetic, optical, electromagnetic, infrared, or semiconductor system (or apparatus or device). Examples of a computer-readable medium include a semiconductor or solid state memory, magnetic tape, a removable computer diskette, a random access memory (RAM), a read-only memory (ROM), a rigid magnetic disk an optical disk. Current examples of optical disks include compact disk-read only memory (CD-ROM), compact disk-read/write (CD-R/W) and DVD.

The preceding description and accompanying drawing are intended to be illustrative and not limiting of the invention. The scope of the invention is intended to encompass equivalent variations and configurations to the full extent of the following claims.

What is claimed is:

1. A device for holding tools during an intervention procedure, characterized in the device comprising:
    a holder body in fixed attachment at a distal end of a shape-sensing fiber optic tether;
    a plurality of tools are stored in said holder body;
    an actuation device within the holder body comprising a plurality of actuators operably connected to corresponding ones of the plurality of tools;
    one of the plurality of tools being deployed by the corresponding actuator through said holder body and held by said holder body in coupled alignment with said shape-sensing fiber optic tether.

2. The device according to claim 1, wherein at least one tool is a sensor, and another tool is deployed in response to readings from said sensor.

3. The device according to claim 1, wherein the one of a plurality of tools is operated by the holder body.

4. The device of claim 3, further comprising a logic device, wherein said logic device activates said one of a plurality of tools.

5. The device according to claim 4, wherein said activation comprises powering a tool action.

6. The device according to claim 5, wherein said activation is triggered by an optical signal through said shape-sensing fiber optic tether.

7. The device according to claim 1, further comprising a processing device and a sensor, wherein said plurality of tools comprise identification, the holder body comprises a chuck holding one of the plurality of tools, and said sensor senses said identification on the one of said tools held in said chuck and sends said identification to said processing device to identify said one of said plurality of tools held in said chuck.

8. The device according to claim 1, further comprising a processing device and a sensor, wherein said plurality of tools comprise identification, and said sensor senses said identification and said processing device uses said identifications to select a one of said tools.

9. The device according to claim 1, further comprising a photo transceiver adjacent a distal end of the optic fiber for sending and receiving data through the optic fiber.

10. The device according to claim 1, further comprising a chamber for collecting samples.

11. A system for performing an intervention, the system comprising:
    a shape sensing fiber optic tether;
    at least one processor; and
    at least one memory operably connected with the at least one processor; characterized in
    a tool holder fixed to a distal end of said shape-sensing fiber optic tether; and
    a plurality of tools fiber optic tether; wherein the processor initiates an action of at least one of the plurality of tools; and
    an actuation device within the holder body comprising a plurality of actuators operably connected to corresponding ones of the plurality of tools;
    one of the plurality of tools being deployed by the corresponding actuator through said holder body and held by said holder body in coupled alignment with said shape-sensing fiber optic tether.

12. The system according to claim 11, wherein the tool holder comprises a chuck and the tool holder deploys one of the plurality of tools through the chuck in response to a signal from the processor.

13. The system according to claim 11, wherein the processor selects one of the plurality of tools.

14. The system according to claim 11, wherein the action is communication of data from the at least one tool.

* * * * *